United States Patent [19]
Gijbels et al.

[11] Patent Number: 5,532,265
[45] Date of Patent: Jul. 2, 1996

[54] TREATMENT OF CENTRAL NERVOUS SYSTEM INFLAMMATORY DISEASE WITH MATRIX METALLOPROTEASE INHIBITORS

[75] Inventors: Koenraad Gijbels, Menlo Park; Lawrence Steinman, Palo Alto, both of Calif.

[73] Assignee: The Board of Trustees of the Leland Stanford Junior University, Stanford, Calif.

[21] Appl. No.: 348,262

[22] Filed: Nov. 30, 1994

[51] Int. Cl.$^6$ ................................. A61K 31/405
[52] U.S. Cl. ........................................... 514/419
[58] Field of Search .................................. 514/419

[56] References Cited

U.S. PATENT DOCUMENTS

| | | | |
|---|---|---|---|
| 5,268,384 | 12/1993 | Galardy | 514/419 |
| 5,270,326 | 12/1993 | Galardy et al. | 514/323 |

OTHER PUBLICATIONS

Gijbels, et al., Gelatinase in the Cerebrospinal Fluid of Patients With Multiple Sclerosis and Other Inflammatory Neurological Disorders, Journal of Neuroimmunology, 41 (1992) 29–34.

Gijbels, et al., Gelatinase B is Present in the Cerebrospinal Fluid During Experimental Autoimmune Encephalomyelitis and Cleaves Myelin Basic Protein, Journal of Neuroscience Research 36:432–440 (1993).

Gijbels, et al., Gelatinase B Producing Cells in Mulitiple Sclerosis Lesions, J. Cell. Biochem. Suppl. 18D:143 (1994).

Grobelny, et al., Inhibition of Human Skin Fibroblast Coolagenase, Thermolysin, and Pseudomonas Aeruginosa Elastase B Peptide Hydroxamic Acids, Biochemistry, vol. 31, No. 31, 76152–54 (1992).

Galardy, et al., Low Molecular Weight Inhibitors in Corneal Ulceration, Annals New York Academy of Sciences, 732:315–323 (1994).

Schultz, et al., Treatment of Alkali–Injured Rabbit Corneas With a Synthetic Inhibitor of Matrix Metalloproteinases, Investigative Ophthalmology & Visual Science, vol. 33, No. 12, 3325–3331 (Nov. 1992).

Galardy, et al., Inhibition of Angiogenesis by the Matrix Metalloprotease Inhibitor N–[2R–2–(Hydroaxamidocarbonymethyl)–4–Methylpentanoyl)] –L–Tryptophan Methylamide, Cancer Research 54, 4715–4718 (Sep. 1, 1994).

Bendeck, et al., Smooth Muscle Cell Migration and Matrix Metalloproteinase Expression After Arterial Injury in the Rat, Circulation Research, vol. 75, No. 3 (Sep. 1994).

*Primary Examiner*—Phyllis G. Spivack
*Attorney, Agent, or Firm*—Bertram I. Rowland; Pamela J. Sherwood

[57] ABSTRACT

A synthetic inhibitor of matrix metalloproteases, the tripeptide hydroxamate GM 6001, is administered to a patient suffering from an inflammatory disease of the central nervous system wherein the effect is mediated primarily through restoration of the blood-CNS barrier.

10 Claims, 3 Drawing Sheets

Time (Days relative to onset of relapse)

TREATMENT OF CENTRAL NERVOUS SYSTEM INFLAMMATORY DISEASE WITH MATRIX METALLOPROTEASE INHIBITORS

This invention was made with Government support under NIH Grant No. 18235. The Government has certain rights in this invention.

INTRODUCTION

1. Technical Field

The subject invention concerns the use of inhibitors of matrix metalloproteases in the treatment of symptoms associated with central nervous system inflammatory disease.

2. Background

The central nervous system is subject to a number of inflammatory diseases, among them multiple sclerosis (MS), various forms of meningitis, and encephalitis. Proteolytic enzymes are believed to contribute to the inflammatory tissue damage in these diseases. Particularly with MS, breakdown of the blood-brain and blood-cerebrospinal fluid (CSF) barrier and inflammatory perivascular infiltration are among the first events in lesion formation and may be followed by demyelination and astrogliosis.

It has been previously shown that gelatinase B is present in the CSF of mice and humans with various inflammatory demyelinating diseases. It is a type IV collagenase, belonging to the family of matrix metalloproteases, as shown by its molecular weight and inhibition profile. Type IV collagen is one of the main components of the basement membrane surrounding capillaries. Disruption of the basement membrane has been associated with breakdown of the blood-brain barrier. Gelatinase B has also been shown to proteolytically cleave myelin basic protein, a key component of the central nervous system.

Diseases of the central nervous system may affect the brain or the spinal cord. Actual analysis of brain or spinal cord tissue is difficult, and so cerebrospinal fluid (CSF) sampling is widely used as an indicator for central nervous system evaluation. The CSF protects the brain and provides for metabolic exchange of nutrients and waste. Anatomically a barrier is formed at the contact between the choroid plexus epithelium and the endothelium of all the capillaries in contact with the CSF. This barrier regulates the passage of substances between the blood and CSF. The blood-brain and blood-CSF barrier is a critical component when evaluating therapies directed at neural disease.

The nature of the blood-CSF and blood-brain barrier, and their experimental manipulation are of great interest medically and scientifically. Compounds which are able to restore barrier integrity, or prevent its loss, have therapeutic and research utility.

3. Relevant Literature

K. Gijbels et al. (1992) *J. Neuroimmunology* 41:29–34 discloses the presence of gelatinases in the cerebrospinal fluid of patients with multiple sclerosis and other inflammatory neurological disorders. K. Gijbels et al. (1993) *J. Neuroscience Res.* 36:432–440 discloses the presence of gelatinase B in the cerebrospinal fluid during experimental autoimmune encephalitis. Gijbels and Steinman, *J. Cell. Biochem. Suppl.* 18D:143 demonstrates that the gelatinase producing cells in MS lesions are from both the immune and nervous system.

The inhibition of collagenase with the hydroxamic acid GM 6001 is described in D. Grobelny et al. (1992) *Biochemistry* 31:7152–7154. The reactivity against various metalloproteases is shown in R. Galardy et al. (1994) *Ann. N.Y. Acad. Sci.* 732:315–323. The treatment of alkali-injured rabbit corneas with GM 6001 is disclosed in G. Shultz et al. (1992) *Invest. Ophth. & Vis. Sci.* 33:3325–3331 and in U.S. Pat. No. 5,270,326. Gm 6001 is shown to inhibit angiogenesis in R. Galardy et al. (1994) *Cancer Res.* 54:4715–4718 and U.S. Pat. No. 5,268,384, and smooth muscle migration in M. Bendeck et al. (1994) *Circ. Res.* 75:539–545.

The metalloprotease activity of neurite growth regulatory factors is disclosed in International patent application WO 90/05 19 1.

SUMMARY OF THE INVENTION

Methods are provided for reducing symptoms associated with matrix metalloprotease (MMP) expression during the course of central nervous system inflammatory disease. Protease inhibitors of matrix metalloproteases are administered systemically, and reduce the level of MMP activity. The treatment provides for an improvement in the abnormal permeability of the blood-CNS barrier associated with such protease activity.

DESCRIPTION OF THE SPECIFIC EMBODIMENTS

Figure 1:
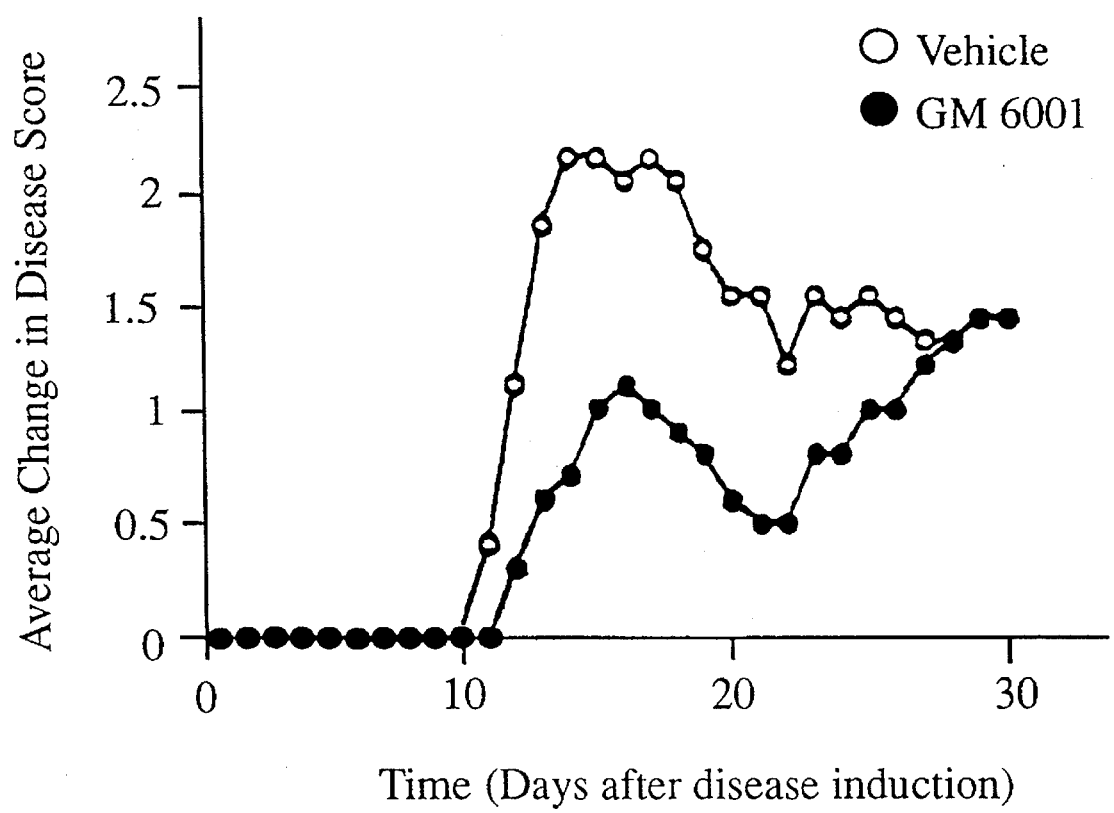
FIG. 1 is a graph showing the effect of GM 6001 inhibitor on the development of EAE clinical symptoms.

Methods are provided to reduce the adverse effects of disease associated matrix metalloprotease (MMP) activity in the spinal cord and brain during central nervous system (CNS) inflammatory disease. Specific inhibitors of MMP activity are administered systemically to patients. Particularly, the loss of blood-CNS barrier integrity associated with inflammatory disease is significantly reduced.

The subject methods provide a means for therapeutic treatment and scientific investigation of the symptoms associated with elevated MMP activity during the progression of inflammatory diseases of the central nervous system. The subject methods are effective in preventing the onset of disease, as well as reversing the disease progression after initial clinical symptoms have appeared, and after the recurrence of symptoms. The ability to reverse symptoms, particularly those related to increased permeability of the blood-CNS barrier, permits the investigation of the role that MMPs and the barrier play in inflammatory central nervous system disease. The term blood-CNS barrier will be used generally to refer to both the blood-brain barrier and the blood-CSF barrier. In most cases, samples from the cerebrospinal fluid (CSF) will used to estimate the biological status of the spinal cord and brain.

Suitable patients for therapeutic treatment are those suffering from inflammatory central nervous system diseases. Inflammatory diseases caused by bacterial and viral infection include viral meningitis and bacterial meningitis, and may also be demyelinating, as with herpes encephalitis and viral meningoencephalitis. Other inflammatory demyelinating diseases are multiple sclerosis (MS) and experimental autoimmune encephalitis (EAE). Diseases of interest will also include inflammatory response to vaccination, particularly rabies vaccine, varicella zoster vaccine, measles vaccine, etc. Of particular interest are multiple sclerosis, and its corresponding animal model, EAE. Mammalian species susceptible to inflammatory CNS diseases include canines and felines, particularly for rabies vaccination; equines, particularly for equine infectious encephalitis; bovines; ovines; etc. and primates, particularly humans. Animal models, particularly small mammals, e.g. murine, lagomorpha, etc. are of interest for experimental investigations.

For the most part, patients suitable for the subject treatment will have raised levels, as compared to a normal control, of a disease associated matrix metalloprotease (MMP), e.g. neutrophil collagenase (EC 3.4.24.23); gelatinase A (EC 3.4.24.24); gelatinase B (EC 3.4.24.35); stromelysin-1 (EC 3.4.24.17); stromelysin-2 (EC 3.4.24.22); matrilysin (EC 3.4.24.23) and interstitial collagenase (EC 3.4.24.7), etc., in the central nervous system. Of particular interest are patients with raised levels of gelatinase B.

The level of disease associated MMP may be detected by any convenient method. Generally, a sample of cerebrospinal fluid (CSF) will be used as to estimate the MMP concentration in the central nervous system. The sample will be taken from the patient by spinal tap, etc., and compared to a normal CSF sample. The presence of the disease associated MMP may be detected by a specific binding assay, particularly immunoassay, e.g. RIA, ELISA, western blot, or by binding to specific substrates or inhibitors. Alternatively, the disease associated MMP may be detected by a functional assay for protease activity, e.g. gel electrophoresis and zymography (see Gijbels et al. [1992]), particularly coupled with verification by addition of specific protease inhibitors, e.g. 1,10-phenanthroline, EDTA, etc., or by degradation of specific substrates. The level of the specific MMP enzymatic activity will usually be at least about 10 fold above normal, more usually at least about 100 fold above normal, and may be as much as about 10,000 fold higher than normal.

For prophylactic treatment, it may not be necessary to demonstrate elevated levels of a disease associated MMP. Prophylaxis will be used in conjunction with an established disease, particularly chronic relapsing disease, such as MS, or with vaccination. Standard clinical criteria may be used to determine patient suitability for treatment. Criteria to establish a diagnosis of MS will generally include the establishment of at least two lesions different in time or space, indicated by neurological dysfunction such as visual difficulties, numbness of fingers, hands and forearms, pain and tingling in feet, distal diminution of sensation, minor motor neuron signs confined to the feet and diminished ankle reflexes, difficulty walking, spasticity in legs, weakness and uncoordinated legs, paresis, paralysis, and the like. Criteria may also include the presence of lesions in magnetic resonance imaging, nerve conduction studies, the presence of IgG in the cerebrospinal fluid, etc.

The subject methods employ compounds that are effective in inhibiting the activity of matrix metalloproteases. Compounds useful in the subject methods will have a $K_i$ of not less than about 0.01 μM, usually not less than about 1 nM, and preferably not less than about 0.5 nM for the disease associated MMP. Preferably, the compound will be substantially specific for MMPs, e.g. the $K_i$ will be at least about 1 μM, preferably at least about 500 μM for proteases such as plasmin, angiotensinase converting enzyme etc. See Grobelny et al. (1992), infra. As an example, the $K_i$ of GM 6001 for gelatinase B is 0.2 nM.

Exemplary of MMP inhibitors are peptide hydroxamates or hydroxamic acids, (as described in U.S. Pat. No. 5,268, 384, herein incorporated by reference) having the formula: QCH2CH(i-Bn)CONHCHR'4COOH, YQ'CON(R3)CHR4COX or R7ONR6COQ'CON(R3)CHR4COX, wherein Q=HONHCONH or ROOC; Q1=(CHR1)nCHR2 or (CHR1)m—C(R1)=C(R2); R=H or 1–6C alkyl; R4'=(3-indolyl) methylene; each R1=H or 1–8C alkyl; each R2=H or 1–8C alkyl; or R1+R2= (CH2)p; p=3–5; R3 =H or 1–4C alkyl; R4=fused or conjugated bicycloaryl methylene (optionally substituted); n=0, 1 or 2; m=0 or 1; X=OR5, NHR5, a cyclic amine or heterocyclic amine residue, or an amino acid residue (or corresponding amide); R5 = H or optionally substituted 1–12C alkyl, 6–12C aryl or 6–16C aryl-alkyl; R6=H or 1–4C alkyl; R7=H, 1–4C alkyl or acyl; Y=H, 1–4C alkyl or acyl; and Y=R7ONR6CONR6, (R6)2NCONOR7 or R6CONOR7. The CONR3 group is optionally replaced by CH2NR3, CH2CHR3, CH=CR3, COCHR3, CH(OH)CHR3, NR3CO or CF=CR3. Of particular interest is the hydroxamate: N-[2(R)-2-(hydroxamido carbonylmethyl)-4-methylpentanoyl]-L-tryptophan methylamide (GM 6001 ).

The MMP inhibitor will generally be administered in an amount sufficient to reduce the enzymatic activity of the disease associated MMP by at least about 25%, more usually by at least about 50%, and may be reduced by as much as 99% or more. The expected reduction of activity may be calculated by determining the level of disease associated MMP in the CSF, determining the level of inhibitor in the CSF after administration, and in vitro calculations of enzyme inhibition. Direct determination of MMP inhibition in the CNS is not necessary. Where administration is prophylactic, the dosage may be determined by extrapolation from MMP levels associated with the particular condition being treated.

The exact dosage will depend on the disease, permeability of the blood-CNS barrier, inhibitor, general health of the patient, the response of the patient to the drug, whether the compound is used by itself or in combination with other drugs, and the like. Generally, the dosage will be sufficient to provide a concentration in the cerebrospinal fluid of at least about the $K_i$ of the inhibitor for the disease associated MMP, usually at least about $10K_i$ of the inhibitor, more usually at least about $100K_i$ of the inhibitor. The concentration will be maintained for at least about 3 hours after administration, usually at least about 6 hours, and may be maintained for at least about 12 hours.

In an experimental model, treatment may be started on induction of the disease, at birth if the disease is congenital, or at a later time point when symptoms become apparent. For clinical use, treatment will be started prophylactically, as previously described, or after increased levels of disease associated MMP in the CSF have been determined. Preferably treatment will be initiated as soon as possible in the course of the disease. The subject compositions may be administered by injection or by implantation of a sustained release formulation such a polymeric matrix, pump, etc. (Heller, *Biodegradable Polymers in Controlled Drug Delivery*, in: CRC Critical Reviews in Therapeutic Drug Carrier Systems, Vol. 1, CRC Press, Boca Raton, Fla., 1987, pp 39–90, describes encapsulation for controlled drug delivery, and Di Colo (1992) *Biomaterials* 13:850–856 describes controlled drug release from hydrophobic polymers). Administration by injection may be daily; one or more times daily, usually not more than about four times, particularly depending upon the level of drug which is administered. Injections may be intraperitoneal, subcutaneous, intramuscular, intravenous, etc. Subcutaneous administration may be less frequent than intravenous administration. Systemic administration is preferred to minimize trauma to the central nervous system.

For the treatment of acute diseases, such as bacterial or viral meningitis and encephalitis, the treatment will be continued until the course of infection has finished. The infection may be monitored by pleocytosis of the CSF. For prophylactic treatment with vaccination, a single dose may be sufficient, or treatment may be continued for several days or weeks. Chronic diseases will require continued treatment, as the effect of the inhibitor is reversable.

Formulations for injection will comprise a physiologically-acceptable medium, such as water, saline, PBS, aqueous ethanol, aqueous ethylene glycols, or the like. A single inhibitor may be used, or a cocktail of two or more inhibitors. Water soluble preservatives which may be employed include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents which may be employed are alkali or alkaline earth carbonates, phosphates, bicarbonates, citrates, borates, acetates, succinates and the like, such as sodium phosphate, citrate, borate, acetate, bicarbonate and carbonate. Additives such as carboxymethylcellulose may be used as carrier in amounts of from about 0.01 to about 5% by weight.

The decreased activity of the disease associated MMP is associated with a reduction in permeability of the blood-CNS barrier. The barrier is compromised during pathogenesis of inflammatory demyelinating disease. The increased permeability may be determined by several methods. Experimentally, the permeability of a dye, such as Evan's blue, may be measured in a control and diseased individual, taking samples from the spinal cord and brain. Alternatively, an enzyme capable of producing a detectable signal, such as horseradish peroxidase may be injected into the blood, and its presence in the brain and spinal cord monitored. Clinically, permeability may be assessed by hematologic evaluation of the patient CSF (see Clinical Hematology, ed. Lotspeich-Steininger et al. [ISBN 0-397-54806-0] pp 394–402), or by gadolinium enhanced magnetic resonance imaging. The abnormal permeability of the blood brain barrier will usually be reduced by at least about 10%, and more usually at least about 25%, and may be reduced by at least about 50%. Clinical assessment of improvement may rely on assessment of CNS lesion size and number.

Associated with the reduction of disease associated MMP activity and reduction in permeability of the CSF-blood barrier, improvement in other disease symptoms may be noted. In MS and EAE, the clinical severity of paresis and paralysis may be reduced. Inflammation in the brain and spinal cord may also be reduced. Particularly when the disease associated MMP is gelatinase B, which is known to cleave myelin basic protein, decreased demyelination may be observed in long term therapy.

The subject methods may be combined with other therapies. For the treatment of MS and EAE, therapies which intervene with the autoimmune associated ternary complex of T cell receptor, major histocompatibility complex and antigert may be used to augment the subject methods (see, for example PCT/US91/02991 ). Administration of interferon β has also been shown to improve the clinical prognosis of MS patients, and may be used in conjunction with MMP inhibitors. Generally, the subject treatment will not interfere with therapies directed at decreasing the autoimmune response. The additional drugs may be administered separately or in conjunction with the MMP inhibitor and may be formulated in the same formulation.

The following examples are offered by way of illustration and not by way of limitation.

EXPERIMENTAL

METHODS

EAE induction, Female SJL/J mice (Jackson Laboratory, Bar Harbor, Me.) were used at 5–7 week of age. EAE was actively induced by subcutaneous immunization with 200 μg of the encephalitogenic proteolipid protein peptide, PLP aa139–151 in CFA plus 0.2 mg Mycobacterium nuberculoris H37RA (Difco Laboratories, Inc., Detroit, Mich.). PLP peptide 139–151 was prepared by continuous flow solid phase synthesis according to the sequence (SEQ ID NO 1 ) HCLGKWLGHPDKF by the Protein and Nucleic Acid Facility, Beckman Center, Stanford, Calif. Peptide purity was examined by HPLC analysis and peptide identity was confirmed by amino-acid composition analysis.

Clinical Scoring of EAE

EAE was scored clinically as follows: no neurological signs=grade 0, weak tail=grade 1, wobbly walk or limb paresis=grade 2, limb paralysis=grade 3, inability to move= grade 4, death=grade 5. Easy access to food and water was provided and animals with grade 3 or 4 received daily parenteral fluid.

Metalloproteinase Inhibitor and Treatment

The peptide hydroxamic acid, N-[2(R)-2-(hydroxamido carbonylmethyl)-4-methylpentanoyl]-L-tryptophan methylamide (GM 6001; Glycomed Inc., Alameda, Calif.) was dissolved in 4% (wt/vol) carboxymethylcellulose in water at concentrations from 10 to 20 mg/ml, and administered by 0.2 ml intraperitoneal injection. The same volume of vehicle was used as a control treatment. Animals were treated daily either from the day of disease induction for 20 d or from the onset of clinical signs for 10 d (randomized for the different treatment groups).

Blood-brain Barrier Permeability

Mice were injected intravenously with 1% (wt/vol) Evans blue (Fisher Scientific Co., Fair Lawn, N.J.) in PBS at a dosage of 4 μl/g body weight. After 1 h the animals were euthanized by $CO_2$ inhalation and perfused with PBS via the left ventricle. Brain and spinal cord were dissected and cut longitudinally. Half of the CNS was used for histopathological evaluation. The other half was weighed and tissue samples were then extracted for 3 d in formamide (5 μl/mg tissue) and the extracts centrifuged for 5 min at 500 g. Evans blue concentration in the extracts was determined by measuring the absorbance at 650 nm. The blood-brain barrier permeability index was calculated by dividing the value for each sample by the corresponding (brain or spinal cord) mean value of four normal noninduced animals.

Histopathology

Brain and spinal cord were fixed for 24 h in 4% (wt/vol) paraformaldehyde in PBS, whereafter they were paraffin embedded and sectioned. Sections were stained with hematoxylin and eosin, Kluver-Barrera and Giemsa stain. Histopathology was assessed as follows. Individual inflammatory lesions were scored as 1=perivascular inflammatory cuff≦three cells thick, 2=>three cells thick. 3=parenchymal infiltrate. The total inflammatory score was then calculated by adding all the scores for individual lesions from all the 5 sections for a given sample. The demyelination score was calculated the same way as inflammatory score, with 1=demyelinated rim around infiltrate, 2=demyelination extending into noninfiltrated tissue.

In vivo inhibitor kinetics. Normal noninduced animals or animals with clinical signs of EAE for 2 d were given a single intraperitoneal injection of 4 mg GM 6001 and euthanized by $CO_2$ inhalation after various time intervals. CSF was taken by suboccipital puncture. Pooled CSF from five animals per time point was frozen immediately at $-70°$ C. GM 6001 concentrations were determined by reversed-phase HPLC by Bay Bioanalytical Laboratories, Richmond, Calif. was diluted into 20% acetonitrile in water and chromatographed on a C-18 reversed-phase column with fluorescence detection. Linearity was determined by spiking blank CSF with increasing amounts of GM 6001. The amount of GM 6001 in CSF samples was calculated based on recovery of GM 6001 and the internal standard in spiked samples. The lower limit for quantification of GM 6001 in the CSF samples was 60 ng/ml.

In vitro inhibition of gelatinase activity. Gelatinase activity in a pooled CSF sample from animals with clinical signs of EAE (grade 2–3 for 4–5 d) was determined by SDS/PAGE zymography. CSF was applied without prior denaturation to a single-well 7.5% (wt/vol) polyacrylamide gel containing 0.1% (wt/vol) SDS to which 0.1% (wt/vol) tissue culture grade gelatin (Sigma Chemical Co., St. Louis, Mo.) was added and copolymerized. The stacking gel was 5% (wt/vol) polyacrylamide and did not contain gelatin. The gel (7 cm×10 cm×0.75 mm) was run for approximately 2 h at 20 mA. After electrophoresis the gel was washed (washing buffer: 50 mM Tris-HCL, 10 mM $CaCl_2$, 0.02% (wt/vol) $NaN_3$, 2.5% (vol/vol) Triton X-100, pH 7.5) to remove the SDS and sliced into strips. The resulting strips were incubated separately at 37° C. during 24 h (same buffer as for the washing, containing only 1% [vol/vol] Triton X-100) for development of the enzyme activity, stained with Coomassie brilliant blue R-250 and destained in methanol/acetic acid. Gelatinase activity was detected as unstained bands on a blue background. To assess the effect of protease inhibitors on the gelatinase activity present in the CSF, metalloprotease inhibitors (dissolved in DMSO) were added to the incubation buffer. GM 6001 was used at final concentrations from 0.1 to 33 μM; 1,10-phenanthroline (Sigma Chemical Co.) was used as a positive control at 2.5 mM, and the noninhibitor lane was incubated in 0.5% (vol/vol) DMSO.

Statistics

The nonparametric Mann-Whitney U-test was used.

RESULTS

The in vitro test of GM 6001 on gelatinase activity in the CSF from animals with EAE showed that gelatinase A and B were both present in the CSF and were equally well inhibited by GM 6001. GM 6001 completely inhibited all gelatinase activity at a concentration of 1 μM to 33 μM; there was partial inhibition at 0.1 and 0.33 μM. The metalloprotease inhibitor phenanthroline (2.5 mM) served as an inhibitory control.

A single intraperitoneal dose of 4 mg GM 6001 gave detectable levels of GM 6001 in the CSF of animals with EAE, measured by reverse phse HPLC, starting 30 min after injection and continuing for at least 4 h. Concentrations were between 100 and 200 ng/ml for at least 3 h, which is in the 0.25–0.50 μM range. After 8 hours the concentration in the CSF was 100 ng/ml. After 16 hours the concentration was below 60 ng/ml. In contrast, GM 6001 concentrations in the CSF of normal noninduced animals never rose above the detection limit after injection of the same dose of the inhibitor.

Three different treatment schedules were used: (a) treatment from disease induction (to evaluate a possible preventive effect), (b) treatment from the onset of clinical signs (to evaluate a possible disease reversing effect) and (c) treatment of established disease during a relapse. Animals that were treated with vehicle showed the typical EAE clinical course. Clinical signs compatible with an ascending myelitis started from day 10–12 after induction and disease peaked around day 14–17, whereafter a variable degree of recovery followed. Several animals went into a clinical relapse from day 20 onwards, after previous partial or complete recovery.

FIG. 1 shows the preventive effect of GM 6001 on the development of EAE. Animals were treated from disease induction for 20 d with vehicle or GM 6001 2×2 mg/d intraperitoneally. Clinical signs were scored as described in Methods. The average change in disease score (relative to the first day of treatment) is given for 10 animals in each treatment group. The clinical severity of the disease was significantly reduced in the GM 6001-treated group compared with the vehicle-treated group. The differences between the treatment groups became insignificant 2 d after cessation of treatment (sp <0.05, Mann-Whitney U-test) (experiment 1 in Table I).

Figure 2:
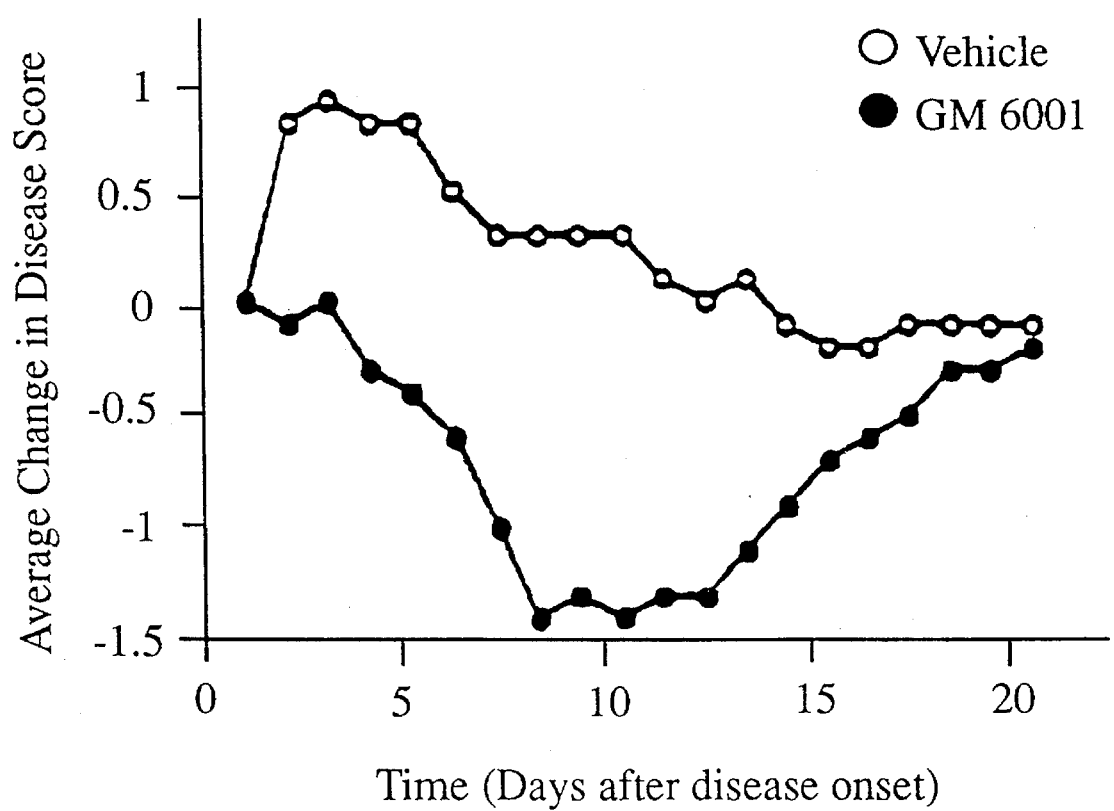
FIG. 2 is a graph showing the effect of GM 6001 inhibitor on EAE clinical symptoms for established disease.

In the second part of this experiment, previously untreated animals were randomly assigned at the onset of clinical signs to be treated either with GM 6001 2×2 mg/d or with vehicle twice a day, for 10 d. In animals treated with vehicle, clinical severity increased for a few days, whereafter the animals slowly recovered (Table I and FIG. 2). In contrast, clinical scores in animals treated with GM 6001 decreased the day after the start of treatment and this difference with the vehicle-treated group remained statistically significant for up to two days after treatment (P<0.005). 8 out of 10 animals treated with GM 6001 returned to score 0 (clinically normal) within 12 d following the onset of clinical signs (compared with 3 out of 10 treated with vehicle), 7 of these animals had a clinical disease relapse during the follow-up period (compared with all 3 treated with vehicle).

In a second experiment, the same treatment schedules were used, but with only one intraperitoneal injection daily and with various doses of the inhibitor. A single daily dose of 4 mg/d had a comparable efficacy as 2×2 mg/d in both treatment schedules (Table I). Doses as low as 0.13 mg/d were still effective if given from disease induction (4 and 1.33 mg/d P<0.005; 0..13 mg/d, P<0.05). When treated from disease onset, there was a clear dose-effect :relationship; only 4 and 1.33 mg/d were significantly effective in reducing disease severity (P<0.05), shown in FIG. 2. Animals treated with GM 6001 recovered faster from the drop in body weight that is associated with the onset of EAE. (It should be noted that animals received parenteral fluid therapy, once they reached a grade 3 clinical score.)

Figure 3:
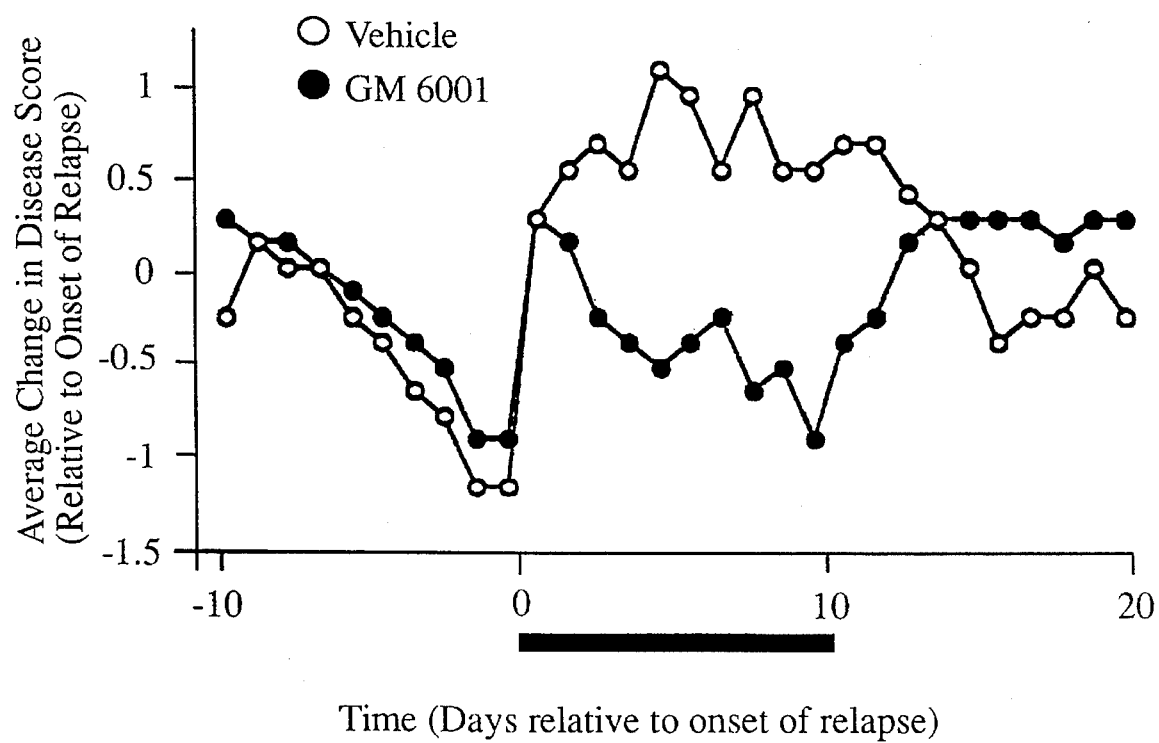
FIG. 3 is a graph showing the effect of GM 6001 inhibitor on EAE clinical symptoms for relapsing disease.

In a third experiment, shown in FIG. 3, a group of nine animals were treated with 1×4 mg/d GM 6001 for 10 days, starting with the onset of clinical relapse. It seen that there is a statistically significant difference in the disease score for the treated group.

It is evident from the above results that treatment of patients suffering from an inflammatory demyelinating dis-

TABLE I

Clinical effect of GM 6001 on EAE

| Group treatment schedule | Treatment | Dose | mg | n | During treatment | After treatment |
|---|---|---|---|---|---|---|
| | | | | | Change in average cumulative score | |
| Experiment 1 | | | | | | |
| From disease induction for 20 d | Vehicle | 2X/d | — | 10 | 16.8 ± 2.06§ | 13.9 ± 3.91 |
| | GM 6001 | 2X/d | 2.00 | 10 | 7.0 ± 2.57§ | 9.9 ± 2.17 |
| From onset of clinical signs for 10d | Vehicle | 2X/d | — | 10 | 5.0 ± 1.99 | −2.7 ± 5.53 |
| | GM 6001 | 2X/d | 2.00 | 10 | −6.5 ± 2.08** | −7.2 ± 2.69 |
| Experiment 2 | | | | | | |
| From discase induction for 20 d | Vehicle | 1X/d | — | 10 | 14.7 ± 1.80 | 20.7 ± 6.06 |
| | GM 6001 | 1X/d | 4.00 | 10 | 2.4 ± 1.16** | 22.2 ± 4.61 |
| | | 1X/d | 1.33 | 10 | 3.4 ± 1.77** | 12.0 ± 3.83 |
| | | 1X/d | 0.40 | 10 | 11.3 ± 0.94 | 23.9 ± 4.96 |
| | | 1X/d | 0.13 | 10 | 7.7 ± 3.09§ | 18.0 ± 9.82 |
| From onset of clinical signs for 10d | Vehicle | 1X/d | — | 8 | 5.1 ± 2.55 | 6.5 ± 10.4 |
| | GM 6001 | 1X/d | 4.00 | 9 | −4.3 ± 2.69 | −7.1 ± 7.86 |
| | | 1X/d | 1.33 | 9 | −4.1 ± 1.81§ | −15.0 ± 5.79 |
| | | 1X/d | 0.40 | 9 | −0.3 ± 2.03 | −7.9 ± 4.44 |
| | | 1X/d | 0.13 | 9 | 2.0 ± 1.92 | −10.6 ± 5.67 |

For clinical scoring, see Methods.
*Change relative to the clinical score at the onset of treatment (mean disease score at the onset of clinical signs for the groups treated from this moment: experiment 1, 1.50 [vehicle] and 1.60 [GM 6001]; experiment 2, 1.63 [vehicle], 1.78 [GM 6001, 4 mg/d], 1.78 [GM 6001, 1.33 mg/d], 1.89 [GM 6001, 0.4 mg/d], 1.56 [GM 6001, 0.13 mg/d]). §P < 0.05. **P < 0.005 compared with vehicle-treated animals (Mann-Whitney U-test).

The degree of inflammation and demyelination was compared histopathologically for animals treated with GM 6001 (1×1.33 mg/d) or with vehicle from the onset of clinical signs (Table II). The inflammatory and demyelination scores were lower after 3 and 10 d of treatment with GM 6001 in all but one group, but the differences did not reach statistical significance. The blood-brain barrier index, however, was significantly elevated after 10 d of disease in the vehicle-treated animals but was normal in the GM 6001 group (P<0.05).

ease with a matrix metalloprotease inhibitor is effective in reducing the disease-related permeability of the blood brain barrier. The treatment is shown to suppress the development of disease, and to reverse ongoing disease in a dose-dependent manner.

All publications and patent applications cited in this specification are herein incorporated by reference as if each individual publication or patent application were specifically and individually indicated to be incorporated by reference.

TABLE II

Effect of GM 6001 Blood-Brain Pen-seeability and Pathology on EAE

| Treatment | n | Blood Brain Barrier Index§ | | Inflammation∞ | | Demyelination |
|---|---|---|---|---|---|---|
| | | Brain | Spinal Cord | Brain | Spinal Cord | Brain + SC |
| 3 days | | | | | | |
| Vehicle | 4 | 1.2 ± 0.08 | 1.0 ± 0.14 | 47.2 ± 12.3 | 29.0 ± 9.26 | 7.0 ± 1.68 |
| GM 6001* | 3 | 1.1 ± 0.16 | 0.7 ± 0.12 | 31.7 ± 5.17 | 14.7 ± 1.67 | 3.7 ± 0.88 |
| 10 days | | | | | | |
| Vehicle | 4 | 1.8 ± 0.07 | 1.6 ± 0.07 | 26.8 ± 1.25 | 14.5 ± 1.50 | 4.5 ± 1.50 |
| GM 6001 | 4 | 0.8 ± 0.007** | 1.1 ± 0.11 | 21.0 ± 3.14 | 15.0 ± 3.24 | 2.3 ± 0.63 |

§ Ratio of permeability for Evan's blue, ∞ degree of inflammation or ¶ demyelination, calculated as described in the methods.
*1 × 1.33 mg/d intraperitoneally,
**P < 0.05 compared with vehicle-treated animals (Mann-Whitney U-test).

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

---

What is claimed is:

1. A method for diminishing the adverse effects of an inflammatory central nervous system disease associated with elevated matrix metalloprotease (MMP) activity in the central nervous system of a mammalian host, said method comprising:

administering to said host N-[2R-2-(hydroxamidocarbonylmethyl)- 4-methylpentanoyl)-L-tryptophan methylamide (GM 6001), in an amount effective to diminish said adverse effects.

2. A method according to claim 1, wherein said administration is systemic.

3. A method according to claim 2, wherein said amount of GM 6001 provides a concentration of GM 6001 in the cerebrospinal fluid of at least the $K_i$ of GM 6001 for the disease associated MMP for a period of at least about 6 hours after administration.

4. A method according to claim 3, wherein said disease associated MMP is gelatinase B (EC 3.4.24.35).

5. A method according to claim 1, wherein said disease is caused by infection.

6. A method according to claim 1, wherein said disease is caused by vaccination.

7. A method according to claim 1, wherein said disease is demyelinating.

8. A method according to claim 7, wherein said disease is selected from the group consisting of multiple sclerosis, and experimental autoimmune encephalitis.

9. A method for diminishing the adverse effects of multiple sclerosis or experimental autoimmune encephalitis in a mammalian host, said method comprising:

administering to said host the MMP inhibitor N-[2R-2-(hydroxamidocarbonylmethyl)- 4-methylpentanoyl)]-L-tryptophan methylamide in an amount effective to diminish said adverse effects, wherein said MMP inhibitor is administered after the onset or recurrence of clinical symptoms.

10. A method for inhibiting disease associated gelatinase B activity in the central nervous system of a mammalian host susceptible to an inflammatory demyelinating disease wherein said disease is selected from the group consisting of multiple sclerosis and experimental autoimmune encephalitis, said method comprising:

administering systemically to said host a dose of N-[2R-2-(hydroxamidocarbonylmethyl)- 4-methylpentanoyl)]-L-tryptophan methylamide in an amount effective to inhibit the activity of gelatinase B in said cerebrospinal fluid by at least about 25% and to provide a concentration of inhibitor in the cerebrospinal fluid of at least the $K_i$ of the inhibitor for gelatinase B for a period of at least about 6 hours after administration.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

His Cys Leu Gly Lys Trp Leu Gly His Pro Asp Lys Phe
1              5                     10